United States Patent
Itu et al.

(10) Patent No.: US 10,971,271 B2
(45) Date of Patent: Apr. 6, 2021

(54) METHOD AND SYSTEM FOR PERSONALIZED BLOOD FLOW MODELING BASED ON WEARABLE SENSOR NETWORKS

(71) Applicant: Siemens Healthcare GmbH, Erlangen (DE)

(72) Inventors: Lucian Mihai Itu, Brasov (RO); Tiziano Passerini, Plainsboro, NJ (US); Puneet Sharma, Monmouth Junction, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 682 days.

(21) Appl. No.: 15/458,106

(22) Filed: Mar. 14, 2017

(65) Prior Publication Data

US 2017/0293735 A1  Oct. 12, 2017

Related U.S. Application Data

(60) Provisional application No. 62/321,441, filed on Apr. 12, 2016.

(51) Int. Cl.
    *G06G 7/50* (2006.01)
    *G16H 50/50* (2018.01)
    *G06N 20/00* (2019.01)

(52) U.S. Cl.
    CPC .............. *G16H 50/50* (2018.01); *G06N 20/00* (2019.01)

(58) Field of Classification Search
    CPC ................................. G06N 20/00; G16H 50/50
    (Continued)

(56) References Cited

U.S. PATENT DOCUMENTS 6,236,878 B1   5/2001  Taylor et al.
6,647,287 B1  11/2003  Peel, III et al.
(Continued)

FOREIGN PATENT DOCUMENTS

CN  103892818 A   7/2014
CN  104138253 A  11/2014
CN  105474219 A   4/2016

OTHER PUBLICATIONS

C.A. Taylor, et al., "Open Problems in Computational Vascular Biomechanics: Hemodynamics and Arterial Wall Mechanics," Comput Methods Appl Mech. Eng., vol. 198, pp. 3514-3523, 2009.
(Continued)

*Primary Examiner* — Andre Pierre Louis

(57) ABSTRACT

A method and system for personalized blood flow modeling based on wearable sensor networks is disclosed. A personalized anatomical model of vessels of a patient is generated based on initial patient data. Continuous cardiovascular measurements of the patient are received from a wearable sensor network on the patient. A computational blood flow model for simulating blood flow in the patient-specific anatomical model of the vessels of the patient is personalized based on the continuous cardiovascular measurements from the wearable sensor network. Blood flow and pressure in the patient-specific anatomical model of the vessels of the patient are simulated using the personalized computational blood flow model. Hemodynamic measures of interest for the patient are computed based on the simulated blood flow and pressure.

29 Claims, 7 Drawing Sheets

(58) Field of Classification Search
USPC .......................................................... 703/9
See application file for complete search history.

(56) References Cited

U.S. PATENT DOCUMENTS

| | | | |
|---|---|---|---|
| 7,860,290 B2 | 12/2010 | Gulsun et al. | |
| 7,953,266 B2 | 5/2011 | Gulsun et al. | |
| 8,098,918 B2 | 1/2012 | Zheng et al. | |
| 8,157,742 B2 | 4/2012 | Taylor | |
| 8,200,466 B2 | 6/2012 | Spilker et al. | |
| 8,249,815 B2 | 8/2012 | Taylor | |
| 8,311,747 B2 | 11/2012 | Taylor | |
| 8,311,748 B2 | 11/2012 | Taylor et al. | |
| 8,311,750 B2 | 11/2012 | Taylor | |
| 8,315,812 B2 | 11/2012 | Taylor | |
| 8,315,813 B2 | 11/2012 | Taylor et al. | |
| 8,315,814 B2 | 11/2012 | Taylor et al. | |
| 8,321,150 B2 | 11/2012 | Taylor | |
| 8,386,188 B2 | 2/2013 | Taylor et al. | |
| 9,349,178 B1 | 5/2016 | Itu et al. | |
| 2010/0017171 A1 | 1/2010 | Spilker et al. | |
| 2010/0067760 A1 | 3/2010 | Zhang et al. | |
| 2011/0224542 A1 | 9/2011 | Mittal et al. | |
| 2012/0022843 A1 | 1/2012 | Ionasec et al. | |
| 2012/0041301 A1 | 2/2012 | Redel | |
| 2012/0041318 A1 | 2/2012 | Taylor | |
| 2012/0041319 A1 | 2/2012 | Taylor et al. | |
| 2012/0041320 A1 | 2/2012 | Taylor | |
| 2012/0041321 A1 | 2/2012 | Taylor et al. | |
| 2012/0041322 A1 | 2/2012 | Taylor et al. | |
| 2012/0041323 A1 | 2/2012 | Taylor et al. | |
| 2012/0041324 A1 | 2/2012 | Taylor et al. | |
| 2012/0041735 A1 | 2/2012 | Taylor | |
| 2012/0041739 A1 | 2/2012 | Taylor | |
| 2012/0053918 A1 | 3/2012 | Taylor | |
| 2012/0053919 A1 | 3/2012 | Taylor | |
| 2012/0053921 A1 | 3/2012 | Taylor | |
| 2012/0059246 A1 | 3/2012 | Taylor | |
| 2012/0072190 A1 | 3/2012 | Sharma et al. | |
| 2012/0121151 A1 | 5/2012 | Bernhardt et al. | |
| 2012/0150516 A1 | 6/2012 | Taylor et al. | |
| 2012/0203530 A1 | 8/2012 | Sharma et al. | |
| 2012/0243761 A1 | 9/2012 | Senzig et al. | |
| 2013/0054214 A1 | 2/2013 | Taylor | |
| 2013/0064438 A1 | 3/2013 | Taylor et al. | |
| 2013/0132054 A1* | 5/2013 | Sharma .................. G06F 19/00 703/9 |
| 2013/0243294 A1* | 9/2013 | Ralovich ............... G06T 7/0012 382/131 |
| 2013/0246034 A1 | 9/2013 | Sharma et al. | |
| 2014/0058715 A1 | 2/2014 | Sharma et al. | |
| 2015/0112182 A1 | 4/2015 | Sharma et al. | |
| 2015/0164453 A1 | 6/2015 | Choi et al. | |
| 2015/0324962 A1 | 11/2015 | Itu et al. | |
| 2015/0374243 A1 | 12/2015 | Itu et al. | |
| 2016/0196384 A1 | 7/2016 | Mansi et al. | |
| 2016/0210435 A1 | 7/2016 | Neumann et al. | |
| 2016/0306943 A1* | 10/2016 | Choi ...................... A61B 5/72 |
| 2017/0032097 A1 | 2/2017 | Itu et al. | |
| 2018/0078149 A1* | 3/2018 | Fonte ................... G16H 10/40 |

OTHER PUBLICATIONS

Chamuleau et al., "Association between coronary lesion severity and distal microvascular resistance in patients with coronary artery disease," Am J Physiol Heart Circ Physiol, vol. 285, pp. H2194-H2200, 2003.

De Bruyne et al., "Simultaneous Coronary Pressure and Flow Velocity Measurements in Humans," Circulation, vol. 94, pp. 1842-1849, 1996.

H. Vernon Anderson et al., "Coronary Atery Flow Velocity is Related to Lumen Area and Regional Left Ventricular Mass," Circulation, vol. 102, pp. 48-54, 2000.

Itu, Lucian et al., "A Parameter Estimation Framework for Patient-Specific Hemodynamic Computations," Journal of Computational Physics, pp. 316-333, Oct. 22, 2014.

Chinese Office Action dated Dec. 24, 2019 in corresponding Chinese Patent Application No. 201710395678.8.

* cited by examiner

METHOD AND SYSTEM FOR PERSONALIZED BLOOD FLOW MODELING BASED ON WEARABLE SENSOR NETWORKS

This application claims the benefit of U.S. Provisional Application No. 62/321,441, filed Apr. 12, 2016, the disclosure of which is incorporated herein by reference in its entirety.

BACKGROUND OF THE INVENTION

The present invention relates to medical-image based blood flow computations for simulating blood flow in a patient's vessels, and more particularly, to enhancing medical image-based blood flow computations using invasive physiological measurements.

Cardiovascular disease (CVD) is the leading cause of deaths worldwide. Essential hypertension is one of the most common age related chronic cardiovascular disorders, affecting more than one billion people. The World Health Organization considers hypertension to be the most important source of morbidity and mortality among its 19 listed major risk factors affecting global health. By predisposing for heart failure, kidney disease, stroke, and dementia, and the subsequent costs to society, hypertension is a major therapeutic target for improving health and wellbeing of the elderly in low, middle, and high income countries. Hypertension accounts for 54% of strokes and 47% of all ischemic heart events. Blood pressure is typically measured at the brachial artery using the oscillometric method. Unfortunately, due to the presence of arterial wave reflections, central aortic systolic pressure (CASP) is often significantly lower than brachial artery systolic BP (BASP). The person specific nature of pressure amplification results in only moderate correlation between CASP and BASP.

Peripheral arterial disease (PAD) of the lower extremities is a common disease affecting approximately 12 million people in the United States. Atherosclerosis is the major cause of PAD of lower extremities. The prevalence of PAD varies based on the population surveyed and the methodology of computing the ankle-brachial index (ABI). The ABI is an initial screening test to help diagnose and grade the severity of peripheral arterial disease (PAD) in the legs.

Coarctation of the aorta (CoA) is a congenital cardiac defect usually consisting of a discrete shelf-like narrowing of the aortic media into the lumen of the aorta, occurring in 5 to 8% of all patients with congenital heart disease. Patients born with CoA require lifelong medical/surgical care, which includes invasive and non-invasive imaging, drug therapy, and, if the CoA recurs, invasive catheterization or surgical intervention to reduce the blood pressure in the ascending aorta. One technique for assessing the functional severity of the coarctation is to measure the blood pressure differences between the arms and legs.

In recent years, there has been considerable focus on computational approaches for modeling the flow of blood in the human cardiovascular system. Blood flow computations, performed using computational fluid dynamics (CFD) algorithms, when used in conjunction with patient-specific anatomical models extracted from medical images, have been proposed for diagnosis, risk stratification, and surgical planning.

BRIEF SUMMARY OF THE INVENTION

The present invention provides a method and system for performing personalized blood flow computations and extracting hemodynamic measures of interest for a patient based on patient data acquired from wearable sensor networks. Embodiments of the present invention utilize a patient-specific blood flow model of the entire systemic circulation, which is personalized from a set of initial clinical measurements and a set of continuous measurements derived from wearable sensor networks. Since the wearable sensor networks can acquire data continuously, the blood flow model can be personalized for multiple patient states.

In one embodiment of the present invention, a personalized anatomical model of vessels of a patient is generated based on patient data. One or more continuous cardiovascular measurements of the patient are received from a wearable sensor network on the patient. A computational blood flow model for simulating blood flow in the patient-specific anatomical model of the vessels of the patient is personalized based on the one or more continuous cardiovascular measurements from the wearable sensor network. Blood flow and pressure in the patient-specific anatomical model of the vessels of the patient are simulated using the personalized computational blood flow model. One or more hemodynamic measures of interest for the patient are computed based on the simulated blood flow and pressure.

In another embodiment of the present invention, a personalized anatomical model of vessels of a patient is generated based on patient data. One or more continuous cardiovascular measurements of the patient are received from a wearable sensor network on the patient. One or more hemodynamic measures of interest for the patient are predicted based on the personalized anatomical model of the vessels of the patient and the one or more continuous cardiovascular measurements from the wearable sensor network using a trained machine learning model.

These and other advantages of the invention will be apparent to those of ordinary skill in the art by reference to the following detailed description and the accompanying drawings.

DETAILED DESCRIPTION

The present invention provides a method and system for performing personalized blood flow computations and extracting hemodynamic measures of interest for a patient based on patient data acquired from wearable sensor networks. Embodiments of the present invention are described herein to give a visual understanding of the methods for personalized blood flow modeling. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

Embodiments of the present invention perform personalized blood flow computations and extract hemodynamic measures of interest based on patient data acquired from wearable sensor networks. Since these wearable sensor networks can acquire patient data continuously, the blood flow model used to perform the blood flow computations can be personalized for multiple patient states. When data used to personalize the model is acquired under a clinical setting, typically only one set of measurements is available, corresponding to one patient state, and this set of patient measurements may not reflect the true patient state due to phenomena like white coat syndrome. White coat syndrome is a phenomenon in which patients in clinical settings exhibit a blood pressure level higher than their normal blood pressure due to anxiety experienced by patients during a clinical visit. Embodiments of the present invention adjust the personalization of the patient-specific blood flow model based on continuous measurements acquired from wearable sensor networks, which allows the patient-specific blood flow model to be personalized at multiple patient states and allows for correction of the patient-specific model to compensate for inaccurate clinical measurements due to phenomena like white coat syndrome.

Figure 1:
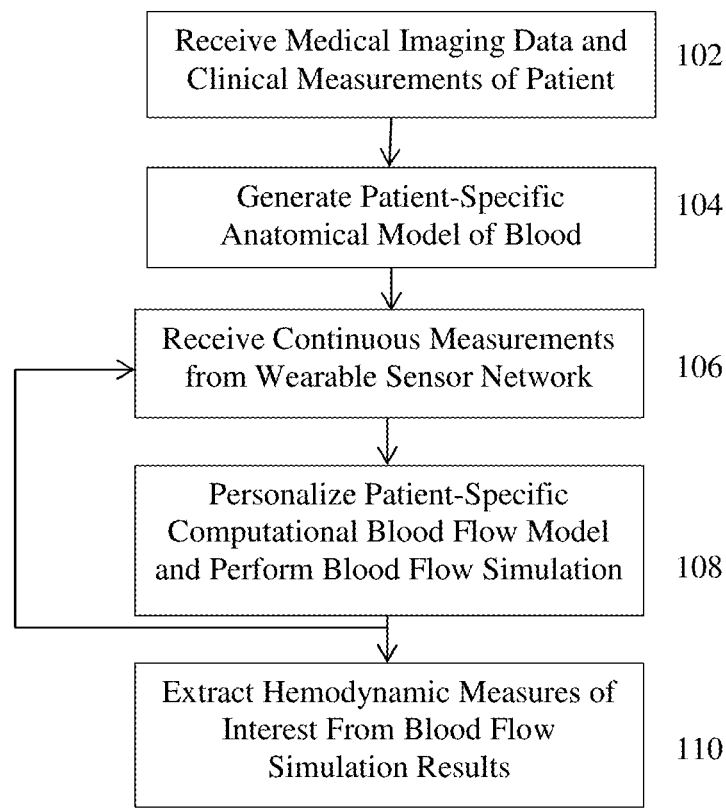
FIG. 1 illustrates a method for performing personalized blood flow computations and extracting hemodynamic measures of interest for a patient according to an embodiment of the present invention.

Embodiments of the present invention utilize a patient-specific computational blood flow model of the entire circulations system or a portion of the circulations system, which is personalized from a set of initial patient measurements and a set of continuous measurements derived from wearable sensors. FIG. 1 illustrates a method for performing personalized blood flow computations and extracting hemodynamic measures of interest for a patient according to an embodiment of the present invention.

At step 102, medical image data and clinical measurements of the patient are received. Medical imaging data from one or multiple imaging modalities can be received. For example, the medical imaging data can include, magnetic resonance imaging (MRI), computed tomography (CT), Dyna CT, Angiography, Ultrasound, echocardiography, Single Photon Emission computed Tomography (SPECT), and any other type of non-invasive medical imaging modality. The medical image data can be 2D, 3D, or 4D (3D+time) medical image data. The medical image data can be received directly from one or more image acquisition devices, such as an MR scanner, CT scanner, Ultrasound device, etc., or the medical image data may be received by loading previously stored medical image data for a patient. Basic patient measurements such as height, weight, body mass index (BMI), length of arms, leg, neck, head, etc., and demographic information, such as gender and age, can be acquired as well. In addition, initial non-invasive clinical measurements, such as the patient's heart rate, systolic and diastolic blood pressure, ECG, etc., may also be acquired.

At step 104, a patient-specific anatomical model of the blood vessels is generated based on the medical image data and/or the clinical measurements of the patient. Initialization measurements are performed based on the medical imaging data or on the basic measurements acquired for the patient, and these measurements are used to perform an initial personalization of the arterial model by defining the patient-specific systemic arterial geometry. Next, at step 106, continuous measurements of patient data are received from a wearable sensor network. These measurements can include quantities like heart rate, blood pressure, pulse oximetry measurements, ECG, etc. These measurements can be continuously received or received at predetermined time intervals, such as every minute or every n minutes. At step 108, a patient-specific computational blood flow model is personalized and run to perform patient-specific blood flow simulations. The measurements received from the wearable sensor network are used together with the previously personalized arterial geometry to personalize the computational blood flow model and run fully personalized blood flow computations. Any type of computational blood flow model can be used in this stage, ranging from lumped-parameter models to one-dimensional, two-dimensional, or three-dimensional models. The computational blood flow model may also be a multi-scale model. The outputs of the hemodynamic computations (blood flow simulations) can include time-varying flow rate, pressure, and cross-sectional area at all locations in the systemic arterial tree, wall shear stress, etc.

At step 110, hemodynamic measures of interest are extracted based on the results of the patient-specific blood flow simulations. The extracted hemodynamic measures of interest may include the central aortic blood pressure, severity of peripheral arterial disease (PAD) (extracted by computing the ankle-brachial index (ABI) from the simulated blood pressures), onset of hypertension, risk of cardiovascular disease (CVD), severity of coarctation (trans-coarctation pressure drop), severity of coronary artery disease (e.g., fractional flow reserve (FFR) measured from the simulated blood pressures in the coronary arteries), etc. The extracted hemodynamic measures of interest may be output by being displayed on a display of a computer device. The extracted hemodynamic measures of interest may also be electronically transmitted to the patient (e.g., to a designated patient device) and/or to a physician or other expert (e.g., to a designated device of the physician) via email, text message, or any other electronic communication protocol. In a possible embodiment, a recommendation for clinical investigation may be automatically issued, for example in response to one or more of the extracted hemodynamic measurements of interest being above a specified threshold. Accordingly, this methodology may allow for a paradigm shift from mainly reactive medicine to more predictive medicine, where the patient is treated based on predictions from the blood flow simulations before the disease reaches a high/critical level of severity. This may not only improve patient outcomes, but also lead to reduced healthcare related costs.

After the personalized blood flow simulation is performed at step 108, the method returns to step 106 and receives new continuous measurements from the wearable sensor network. The patient-specific computational blood model is then personalized again by adjusting parameters of the patient-specific computational blood flow model based on the newly acquired measurements from the wearable sensor network. In an advantageous implementation, a time period (e.g., 1 hour) can be specified and the patient-specific computational blood flow model can be re-personalized and run after every time the specified time period passes using the continuous patient measurements acquired from the wearable sensor network during that time period. The steps of the method of FIG. 1 are described in greater detail below in connection with the embodiment of FIG. 3.

Figure 2:
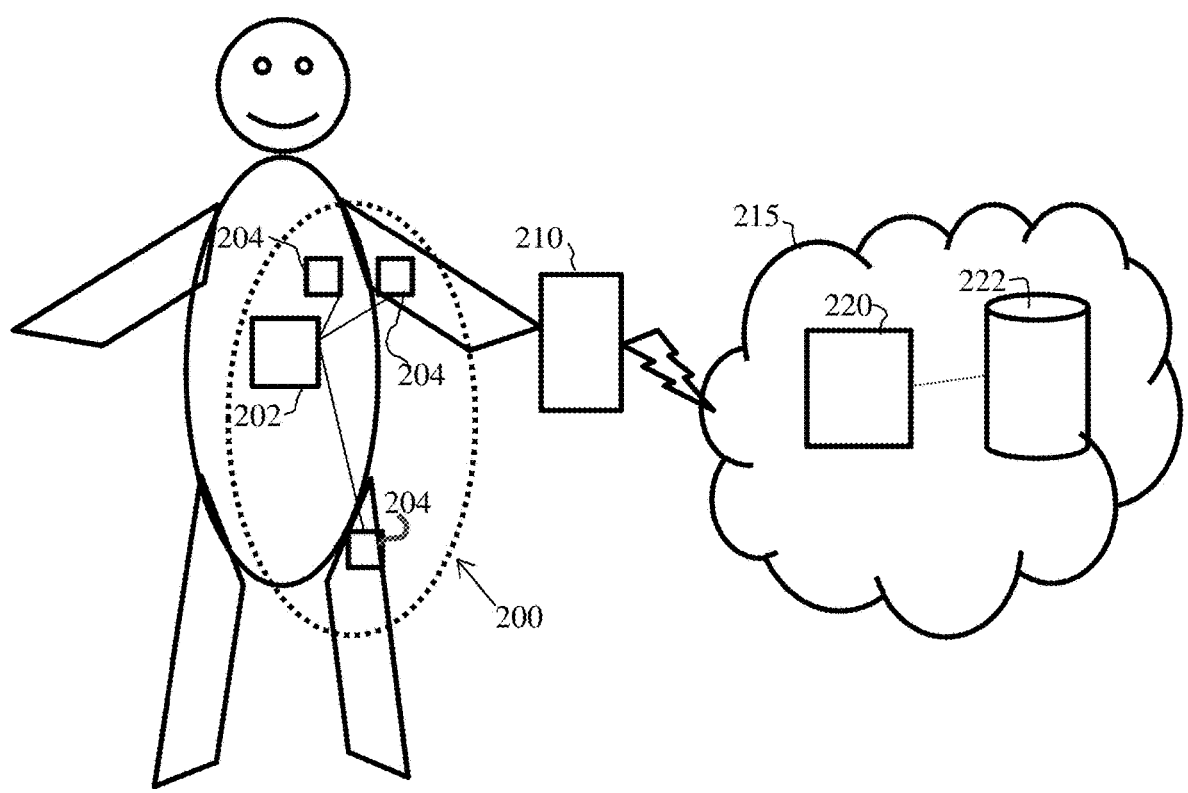
FIG. 2 illustrates a system for performing personalized blood flow computations and extracting hemodynamic measures of interest for a patient according to an embodiment of the present invention.

FIG. 2 illustrates a system for performing personalized blood flow computations and extracting hemodynamic measures of interest for a patient according to an embodiment of the present invention. As shown in FIG. 2, a wearable sensor network 200 is used to acquire various continuous measurements of a patient. The wearable sensor network 200 can be a wearable wireless body area network (BAN), which is used to acquire data related to the person wearing the BAN and possibly the environment surrounding the person wearing the BAN. BANs are a subclass of wireless sensor networks which care employed to monitor the health and physical state of subjects. The wearable sensor network 200 of FIG. 2 includes a control unit 202 and a plurality of sensors 204. Although three sensors 204 are shown in FIG. 2, the present invention is not limited to any particular numbers of sensors. The control unit 202 can include a microprocessor to control operations of the wearable sensor network 202, a transceiver to receive data from the sensors 204 and transmit the data to a user device 210, and a power source (e.g., battery) to provide power to the control unit 202 and possibly to the sensors 204. The sensors 204 are placed at various locations on the patient's body and acquire continuous measurements of the patient. In an advantageous embodiment, the sensors 204 may include a heart rate sensor, one or more blood pressure sensors, an ECG sensor, and a pulse oximeter. The sensors 204 of the wearable sensor network 200 may also include other sensors, such as sensors for measuring a patient's breathing, brain activity (e.g., electroencephalography (EEG)), electromyography (EMG), skin temperature, skin conductance, electrooculography (EOG), blood pH, glucose levels, etc. The sensors 204 may also include one or more inertial sensors (e.g., accelerometers) to detect patient motion. One or more of the sensors 204 may be powered and controlled by the control unit. However, one or more of the sensors 204 may include their own power source (e.g., battery), microprocessor, and transceiver. The control unit 202 receives the patient measurements from the various sensors 204 and transmits the patient measurements to the user device 210. The control unit 202 and the sensors 204 can communicate via a wireless BAN (WBAN) communication protocol, such as IEEE.802.15.6. The control unit 202 can transmit the measurements to the user device 210 using a wireless communication protocol, such as Bluetooth or Zigabee, or via the WBAN communication protocol. In the embodiment of FIG. 200, the wearable sensor network 200 includes a control unit 202 that transmits all of the measurements acquired by the sensors 204 to the user device 210. However, the present invention is not limited thereto, and in an alternative embodiment, the sensors of the wearable sensor network may transmit their respective measurements directly to the user device.

The personalization of the computational blood flow model and blood flow computations using the personalized computational blood flow model can be performed either locally on the user device 210 or by the wearable sensor network 200, or the acquired data may be sent by wireless communication to a central server (cloud) 220 where the processing is performed. That is, in one embodiment, the user device 210 receives the continuous measurements from the wearable sensor network 200 (step 106 of FIG. 1), performs the personalization of the computational blood flow model and the blood flow simulations (step 108), and extracts and outputs the hemodynamic measures of interest (step 110). The user device 210 is a computer device that is local to the patient. The user device 210 can include a processor, memory, storage, user input, display, and network interface. In an advantageous embodiment, the user device 210 is a mobile device, such as a smart phone, tablet, personal digital assistance, etc. The user device 210 can output the extracted hemodynamic measures of interest by displaying the hemodynamic measures of interest of its display, and/or electronically transmitting the hemodynamic measures of interest to a remote device, such as a device associated with a physician. The user device 210 can also display and/or transmit the results of the blood flow simulations, such as curves showing time-varying pressure, flow rate, cross-sectional area, wall shear stress, etc., at various locations in the systemic arterial tree.

In another embodiment, the personalization of the patient specific computational blood flow model and the simulation using the personalized computational blood flow model may be performed all or in part by the wearable sensor network 200. Since the radio component of the wearable sensor network 200 requires a large amount of energy, efficient local processing is important for obtaining a low power system. In a possible implementation, fog computing or mist computing may be used when personalizing and running the computational blood flow model. Fog computing has been introduced to solve crucial challenges in the Internet of Things (IoT), such as bandwidth requirements, application manageability, etc. In fog computing, the applications are run on the gateways (e.g., control unit 202), leading to a simpler coordination and management. However, the gateway may become a single point of failure. Mist computing takes fog computing one step further, whereas the computations are performed on the edges of the network, i.e., at the level of the microcontrollers in the embedded nodes (e.g., sensors 204). Thus, delays are further reduced and the autonomy of the system is increased (it no longer depends on a stable and continuous wireless network).

In another embodiment, the user device 210 transmits the continuous measurements received from the wearable sensor network 200 to the central server 220. For example, the user device 210 can transmit the continuous measurements to the central server 220 via a data network 215, such as the Internet. The central server 220 received the continuous measurements of the patient acquired from the wearable sensor network 200 (step 106 of FIG. 1), performs the personalization of the computational blood flow model and the blood flow simulations (step 108), and extracts and outputs the hemodynamic measures of interest (step 110). The central server 220 may be a computer device including a processor, memory, storage, network interface, and using input/output. In a possible implementation, the central server 220 may be a cloud based computed device that controls other cloud based computer devices. Accordingly, the processing to perform the personalization of the computational blood flow model, blood flow simulations using the computational blood flow model, and the extraction of the hemodynamic measures of interest may be performed by only the central server 220 or may be distributed among multiple cloud based computer devices. The central server 220 can output the hemodynamic measures of interest and possibly the results of the blood flow simulations by transmitting the hemodynamic measure of interest to the user device 210, as well as one or more other remote devices, such as a device associated with a physician.

The central server can store the extracted hemodynamic measurements of interest and simulation results for the patient in a database 222, along with hemodynamic measurements of interest and simulation results for other patients. The central server 220 can perform population studies by performing continuous data analysis on all of the patient data stored in the database 222. In a possible embodiment, the central server 220 can compare in real time hemodynamic measurements of interest extracted for a specific patient to the corresponding measurements acquired on a large population of subject. This information can be used to send feedback to the patient and/or the physician regarding potential deviations from the population-averaged values. Sub-group analysis can be performed by the central server 220 to identify a patient sub-population with statistically similar hemodynamic measurements of interest and to correlate the hemodynamic measurements of interest with health status, medical history, or other demographic parameters based on the identified sub-population.

In another possible embodiment, a hybrid approach can be employed in which a simplified model is run locally on the user device 210 and if the hemodynamic measures of interest are in a certain range (e.g., close to a threshold values), the data may then be sent to a central server/cloud 220 for processing using a more detailed computational model. For example, the more complex computational model on the central server/cloud 220 may be able to provide additional measures of interest other than the ones extracted from the simplified local model. In an exemplary implementation, only the output of the hemodynamic measures of interest may be sent offline to be analyzed by an expert in a case in which a decision cannot be taken locally based on a predefined algorithm. In one possible implementation, the simplified local model is a less detailed computational blood flow model than the complex computational model on the central server/cloud 220. In another possible implementation, the simplified local model can be a machine learning based model (described in greater detail below) and the model on the central server is a computational blood flow model.

Figure 3:
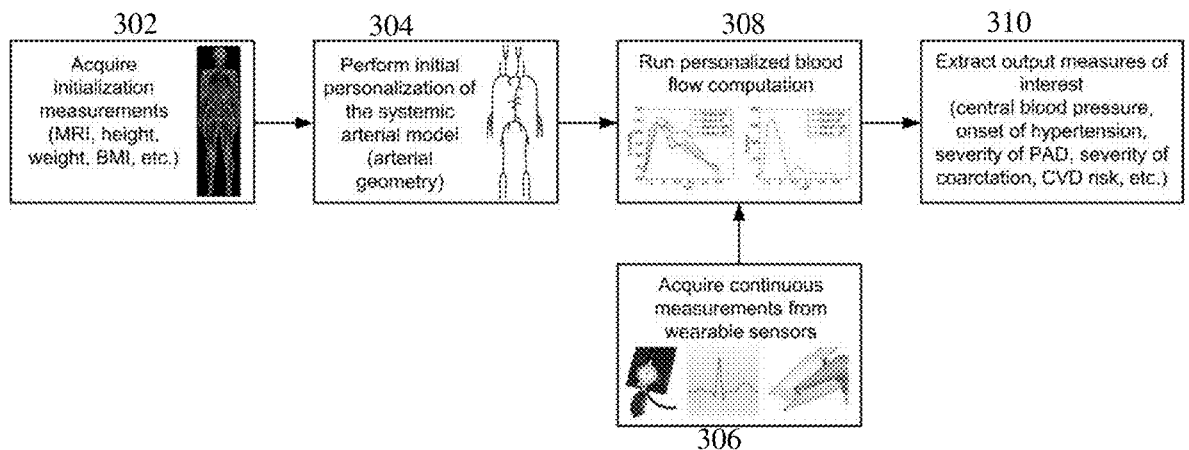
FIG. 3 illustrates a method of performing personalized whole-body blood flow computations and extracting hemodynamic measures of interest for a patient according to an embodiment of the present invention.

FIG. 3 illustrates a method of performing personalized whole-body blood flow computations and extracting hemodynamic measures of interest for a patient according to an embodiment of the present invention. In the embodiment of FIG. 3, the method of FIG. 1 is applied to perform personalized whole-body blood flow computations. Steps 302, 304, 306, 308, and 310 of FIG. 3 correspond to steps 102, 104, 106, 108, and 110 of FIG. 1, respectively, and the description of the method of FIG. 3 provides additional details regarding the respective method steps of FIG. 1 as applied in an advantageous embodiment in which whole-body blow computations are performed.

At step 302, initialization measurement data of a patient is received. The initialization measurement data can include medical image data and/or non-imaging patient measurements. In an advantageous embodiment, the medical image data can be MRI image data acquired in a whole-body MRI scan, as whole-body MRI screening has been reported as being safe and accurate for detecting serious pathology in the asymptomatic general population. The non-imaging patient measurements can include height, weight, BMI, gender, age, length of arms, legs, neck, and head, as well as other possible patient measurements.

Figure 4:
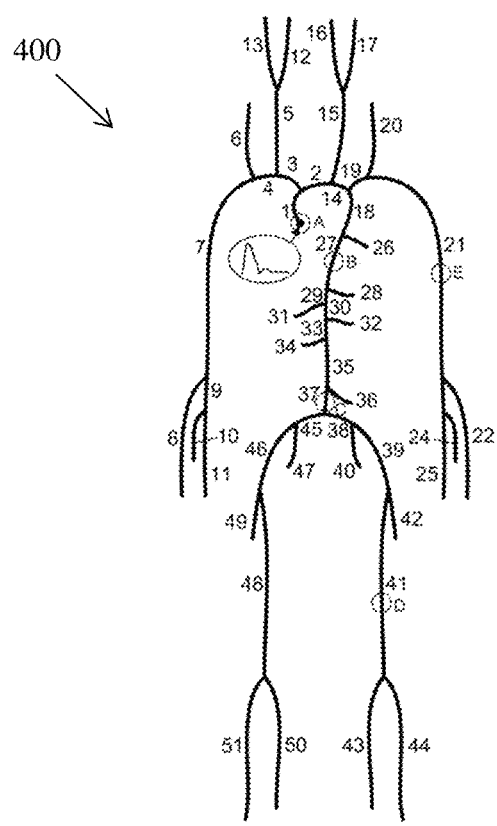
FIG. 4 illustrates an exemplary full-body systemic arterial model according to an embodiment of the present invention.

At step 304, an initial personalization of the system arterial model (i.e., the arterial geometry) is performed. A population averaged whole-body systemic arterial model may be used as a starting point for personalizing the arterial geometry. For example, the population averaged whole body systemic arterial model may be based on an atlas model or previously published arterial models. The lengths and radii of the arteries in the systemic arterial model are then personalized based on the initialization measurement data (e.g., medical image data and/or initial non-imaging measurements) of the patient, resulting in a patient-specific anatomical model of the system arterial geometry. FIG. 4 illustrates an exemplary full-body systemic arterial model according to an embodiment of the present invention. As shown in FIG. 4, the full-body systemic arterial model 400 includes 51 arteries (numbered 1-51).

In one embodiment, the lengths and radii of the arteries in the populations averaged whole-body systemic arterial model can be automatically adjusted based on the basic measurements of the patient including, the height, weight, BMI, gender, length of arms, length of legs, length of neck, length of head, etc. In another embodiment, the lengths and the radii of the arteries in the whole-body systemic arterial model can be personalized based on the medical image data, such as the whole-body MRI scan. For example, a patient-specific anatomical model of the system arterial geometry can be automatically extracted from the medical image data. In order to generate a patient-specific anatomical model of the system arterial geometry, centerlines of the arteries in the systemic arterial model can be extracted in 3D medical image data using an automated vessel centerline extraction algorithm, such as he method described in United States Published Patent Application No. 2010/0067760, which is incorporated herein by reference. Once the centerlines of the arteries are extracted, cross-section contours can be generated at each point of the centerline tree. The cross-section contour at each centerline point gives a corresponding radius and cross-section area measurement at that point in the artery.

Returning to FIG. 3, at step 306, the continuous measurements from the wearable sensors are acquired. The continuous measurements from the wearable sensors can include heart rate, ECG signal, blood pressure measurements at one or more locations, and/or pulse oximetry measurements at one or more locations. In an advantageous implementation, the continuous measurements include brachial-ankle pulse oximetry or pressure measurements and may also include pulse oximetry and/or pressure measurements at other arterial locations, such as the femoral artery and the carotid artery. The more measurements available, the more reliable the personalization will be. The measurements can include measurements associated with multiple different patient states, such as rest, lying down, sitting, upright, different levels of physical exercise, sleep, pre- and post-interventional, etc. The wearable sensor network can automatically distinguish between different states based on relative positions of the sensors and changes in the patient's heart rate, ECG, breathing, etc.

At step 308, the patient-specific computational blood flow model is personalized based on the initial personalized system arterial model (arterial geometry) and the continuous measurements acquired from the wearable sensor network. In an advantageous embodiment of the present invention, a reduced-order computational fluid dynamics (CFD) based model, whose main component is a one-dimensional model, may be used to perform the whole-body blood flow computations. Time-varying flow rate profiles can be used as inlet boundary conditions, while three-element Windkessel models can be coupled at the outlets of the highest order model. To perform the patient-specific computations, the computational blood flow model has to be personalized. In an advantageous implementation, the following components of the computational blood flow model are personalized:

arterial geometry, arterial wall properties, inlet boundary conditions, and outlet boundary conditions. The arterial geometry is personalized during the initial personalization in step 304.

A pulse wave measured using the continuous pulse oximetry measurements can provide time related information such as intravascular pressure transmission, as well as information on the volume change of arterial blood. The arterial wall properties may be personalized using brachial-ankle pulse oximetry or blood pressure measurements. Pulse oximetry or pressure measurements performed at other arterial locations, such as the femoral artery or the carotid artery, can also be used to personalize the arterial wall properties. Based on the transit time estimated from these from these measurements and the ECG signal, several localized pulse wave velocities may be determined and then used to define the arterial wall properties. The more measurements are available, the more reliable the personalization will be.

In an advantageous embodiment, the inlet boundary condition is personalized by generating a personalized time-varying flow rate profile at the aortic inlet (shown at point A in the systemic arterial model 400 of FIG. 4). The cardiac output may be derived continuously using Pulse Wave Transit Time (PWTT), which is obtained by the pulse oximetry and ECG signals from each cycle of the ECG and peripheral pulse wave. This provides a real-time, continuous, and non-invasive cardiac output measurement along with the vital sign parameters of the ECG and SpO2 (peripheral capillary oxygen saturation). This estimated cardiac output can be used together with the measured heart rate to scale a population average aortic inlet profile, so as to provide a personalized flow profile at the inlet of the ascending aorta.

In an advantageous embodiment, the computational blood flow model utilizes three element Windkessel models coupled at the outlets of the system arterial model. For example, three-element Windkessel models can be coupled to the outlets of arteries 6, 8, 10, 11, 12, 13, 16, 17, 20, 22, 24, 25, 26, 28, 29, 31, 32, 34, 36, 40, 42, 43, 44, 47, 49, 50, and 51 in the full-body systemic arterial model 400 of FIG. 4. The outlet boundary conditions are personalized by finding personalized parameters (compliance and resistance) for each of the outlet Windkessel models. The total compliance for the system arterial model may be determined from the pulse pressure information derived from the brachial-ankle pulse oximetry or pressure measurements. The total compliance can then be distributed to the outlets based on the size of the terminal arterial segments. The resistance at each outlet can be determined from a-priori defined flow distributions, which may then be altered based on the physical activity of the patient. For example, in the case of physical exercise, more blood may be directed towards the arms and/or legs depending on the type of activity.

Overall the model personalization framework includes two sequential steps. First a series of parameters are computed directly, and then, a fully automatic optimization based calibration method is utilized to estimate the values of the remaining parameters. The parameter estimation problem is formulated as a numerical optimization problem, the goal of which is to find a set of parameter values for which the objectives are met. Additional details regarding personalization of the full-body system arterial blood-flow model are described in United States Published Patent Application No. 2016/0196384, entitled "Personalized Whole-Body Circulation in Medical Imaging," the disclosure of which is incorporated by reference herein in its entirety.

Once the arterial geometry, arterial wall properties, inlet boundary condition, and outlet boundary conditions are personalized, resulting in a personalized computational blood flow model, a blood flow simulation is performed using the personalized computational blood flow model. In particular, the personalized computational blood flow model computes blood flow and pressure values at each of a plurality of points in the patient-specific systemic arterial model over a plurality of time steps. In an advantageous implementation, the personalized computational blood flow model performs CFD computations of the blood flow and pressure values at each point in the patient-specific systemic arterial model over a plurality of time points based on the personalized inlet flow profile, the personalized wall properties, and the personalized outlet boundary conditions.

Returning to FIG. 3, at step 310, hemodynamic measures of interest are extracted from the simulation results and output. The hemodynamic measures of interest may include the central aortic blood pressure, onset of hypertension, severity of peripheral arterial disease (PAD), severity of coarctation, risk of cardiovascular disease (CVD), severity of coronary artery disease, and/or other hemodynamic measures of interest. The central aortic blood pressure is computed from the simulated blood pressure in the aorta. The severity of peripheral arterial disease (PAD) can be computed by computing the ankle-brachial index (ABI) from the simulated blood pressures. The ABI compares the blood pressure at the ankle with the blood pressure at the arm. The ABI can be computed by calculating a ratio of the simulated blood pressure at the ankle to the simulated blood pressure at the arm. The severity of coarctation can be computed by calculating the trans-coarctation pressure drop from the simulated blood pressures. The severity of coronary artery disease can be computed by calculating fractional flow reserve (FFR) or trans-stenotic pressure drop at various locations in the coronary arteries based on the simulated blood pressures.

In a possible embodiment, risk factors, such as a CVD risk factor and/or a hypertension risk factor can be calculated using a trained machine learning based model based on other hemodynamic measures computed from blood flow and pressure computations by the personalized computational blood flow model. For example, a machine learning based regressor can be trained based on a database of hemodynamic measures of interest extracted from blood flow simulations for a large population of patients to predict a risk score for CVD or hypertension. Various machine learning algorithms, such as deep learning, support vector machine, probabilistic boosting tree, random forests, etc., can be used to train the machine learning based regressor. When the hemodynamic measures of interest are extracted for a particular patient using the personalized computational model, the hemodynamic measures of interest are input as features to the trained machine learning based regressor, and the trained machine learning based regressor calculates a risk score for CVD of hypertension for the patient.

The embodiment of FIG. 3 utilizes a reduced-order CFD based computational model including one-dimensional models of the systemic arteries coupled to lumped Windkessel models at the outlets. Other computational models such as multi-scale models, 3D models, etc., can also be used for full-body systemic arterial blood flow computations. For example, details regarding a multi-scale model for full-body systemic blood flow computations are described in United States Published Patent Application No. 2016/0196384, entitled "Personalized Whole-Body Circulation in Medical Imaging," the disclosure of which is incorporated by reference herein in its entirety.

Figure 5:
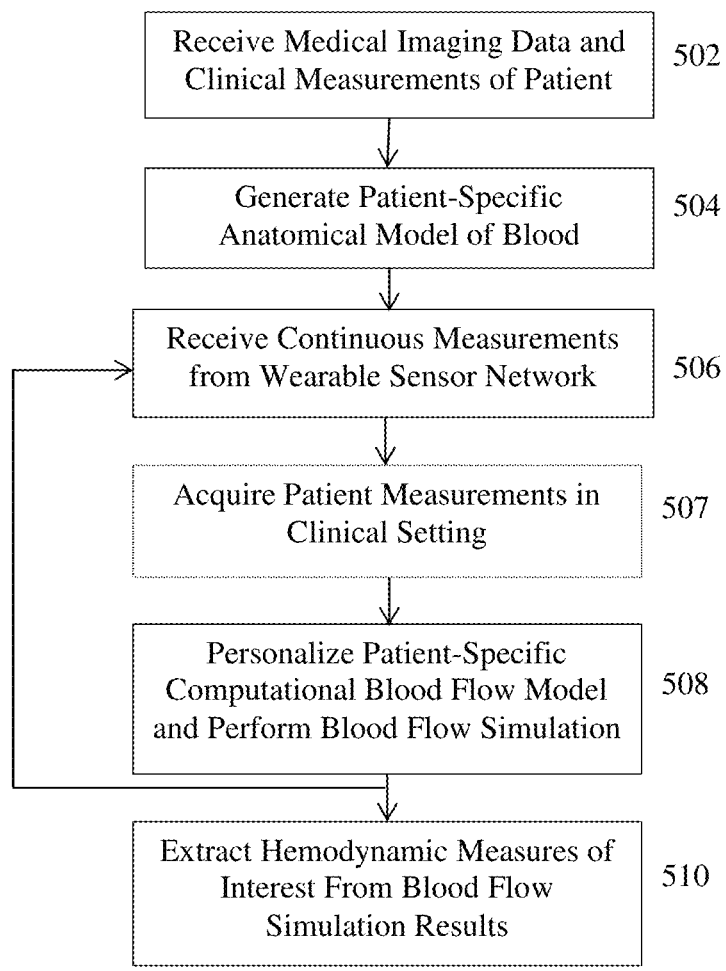
FIG. 5 illustrates a method for performing personalized blood flow computations and extracting hemodynamic measures of interest for a patient according to another embodiment of the present invention.

FIG. 5 illustrates a method for performing personalized blood flow computations and extracting hemodynamic measures of interest for a patient according to another embodiment of the present invention. Since the measurements performed by the wearable sensor network may have some uncertainty or may be insufficient for reliably personalizing the computational blood flow model over a large period of time, clinical measurements may be performed at certain points in time. The method of FIG. 5 provides a method similar to the method of FIG. 1 that is modified to reflect an embodiment in which additional clinical measurements are acquired. Steps 502, 504, 506, 508, and 510 of FIG. 5 are similar to steps 102, 104, 106, 108, and 110 of FIG. 1, respectively. Step 507 is an optional step that is not performed each time the method repeats steps 506 and 508. At step 507, patient measurements are acquired in a clinical setting. These clinical measurements may be performed periodically or at any point in time, and may be different from the clinical measurements performed for the initiation of the arterial model. When the additional clinical measurements are acquired, the patient-specific computational blood flow model is personalized (at step 508) based on these clinical measurements in addition to the continuous measurements from the wearable sensor network. Similar to the initial measurements, these clinical measurements may or may not involve medical imaging techniques. The subsequent clinical measurement acquisitions may be used, for example if the blood flow model also incorporates a model for disease evolution (e.g., fluid-solid-growth modeling), and the periodic clinical measurements may be used in this case to calibrate parameters for the disease evolution. Furthermore, the clinical measurements may be used to calibrate the measurements performed by the wearable sensor network (e.g., to cancel out any bias/offset, etc.). The periodic clinical measurements can also be used to detect malfunctioning (e.g., reduced accuracy of measurements) in the sensors of the wearable sensor network. In a possible embodiment, the clinical measurements may be performed in response to an indication generated based on computations using the wearable sensor measurements (e.g., an internal threshold is exceeded, which indicates a change in the level of disease severity. In this case, the clinical measurements may be used to confirm, infirm, or further investigate the finding. The data thus acquired can then also be used to recalibrate the personalized computational blood flow model.

In an alternative embodiment of the present invention, machine learning based models may be used instead of a computational blood flow model for predicting hemodynamic measures of interest. The machine learning based models may be trained in an offline training stage based on patient or synthetic data. The machine learning based models may be trained using various machine learning algorithms, such as deep learning, support vector machine, etc. For example, the machine learning based models can be trained as described in U.S. Pat. No. 9,349,178, entitled "Synthetic Data-Driven Hemodynamic Determination in Medical Imaging," the disclosure of which is incorporated herein by reference in its entirety. Machine learning based models have the advantage that they are more computationally efficient as compared with computational models, which are typically based on the numerical solution to complex systems of equations. This aspect is advantageous if the application is run on the wearable system, whose power efficiently needs to be maximized. In the case in which trained machine learning based models are used to predict the hemodynamic measures of interest, for each time period for which the hemodynamic measures of interest are recalculated, the continuous measurements from the wearable sensor network for that time period are input as features to the trained machine learning based models, and the trained machine learning based models re-calculate the hemodynamic measures of interest based on the updated set of features. The trained machine learning based models may be trained to directly predict respective hemodynamic measures of interest of may be trained to predict blood flow and pressure in the patient specific anatomical model (e.g., the systemic arterial model), and the predicted blood flow and pressure can then be used to compute predicted hemodynamic measures of interest.

Figure 6:
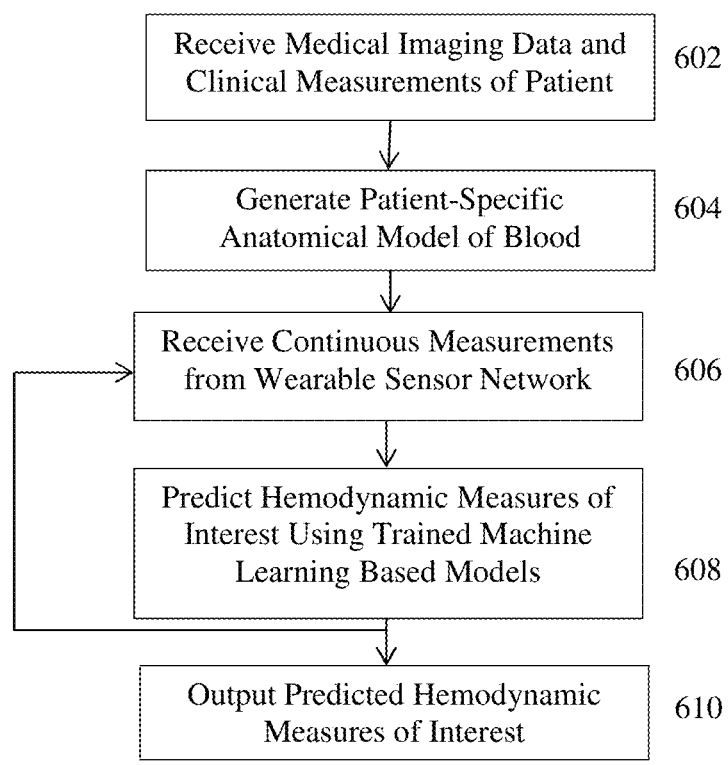
FIG. 6 illustrates a method of machine learning based prediction of hemodynamic measures of interest for a patient based on wearable sensor networks according to an embodiment of the present invention.

FIG. 6 illustrates a method of machine learning based prediction of hemodynamic measures of interest for a patient based on wearable sensor networks according to an embodiment of the present invention. Steps 602, 604, and 606 of FIG. 6 are similar to steps 102, 104, and 106 of FIG. 1. At step 608, the hemodynamic measures of interest for the patient are predicted based on the continuous measurements from the wearable sensor network and the patient-specific anatomical model using trained machine learning based models. In one embodiment, the hemodynamic measures of interest (e.g., central aortic blood pressure, onset of hypertension, severity of peripheral arterial disease (PAD), severity of coarctation, risk of cardiovascular disease (CVD), severity of coronary artery disease) are directly predicted using a respective trained machine learning based model for each hemodynamic measure of interest. In this case, geometric measurements of the patient's arteries and the continuous cardiovascular measurements from the wearable sensor network are input as features to each respective trained machine learning based model, which computed the respective predicted hemodynamic measure of interest based on the input features. In another embodiment, the geometric measurements of the patient's arteries and the continuous cardiovascular measurements from the wearable sensor network are input as features to a trained machine learning based model that is trained to predict blood flow and pressure values at locations in the patient-specific anatomical model based on those features. The hemodynamic measures of interest are then computed based on the predicted blood flow and pressure values. At step 610, the predicted hemodynamic measures of interest are output. The method repeats steps 606 and 608, for example every time a specified time period passes, and every time steps 606 and 608 are repeated the newly received continuous measurements acquired during the time period by the wearable sensor network are added to the set of features, resulting in an updated set of features that is used by the machine learning based models.

In a possible embodiment, methods and system described above can be used as a "personal trainer" that automatically suggest a fitness program based on the available measurements and the hemodynamic measures of interest calculated from the simulated blood flow using the personalized blood flow model. In another possible embodiment, the methods and system described above can be used as a first aid assistance device that suggests a best course of action immediately after an event (e.g., in response to increased pain or swelling in legs due to phlebitis, a suggestion can be generated to assume anti-inflammatory drug and refer to a physician). The recommendation can be generated based on available measurements, computational modeling results/ hemodynamic measures of interest, and an automated analysis of population data (including outcome) from the central server.

The methodology described herein in the above described embodiments may be similarly applied to non-blood flow related medical applications. For example, a wearable sensor network focused on ECG signals may be used for personalizing a computational electrophysiology (EP) model.

The embodiments described above may be used to detect onset of systemic hypertension, particularly in subjects predisposed to developing hypertension (e.g., due to a family history). The embodiments described above may be used to achieve a better understanding of primary systemic hypertension, as its etiology is not well understood and embodiments of the present invention can help to better understand the relationship between hypertension and atherosclerosis and answer which is the cause and which is the effect. The embodiments described above may be used to provide a reliable estimation of central arterial blood pressure, which has generated interest as a tool in predicting cardiovascular events. Moreover, in combination with other measures of atherosclerosis, the estimated central arterial blood pressure can be used to estimate the risk of future events. Embodiments described above can also be used to estimate functional severity of peripheral arterial disease under pre- and post-interventional conditions and/or to estimated functional severity of aortic coarctation under pre- and post-interventional conditions.

Figure 7:
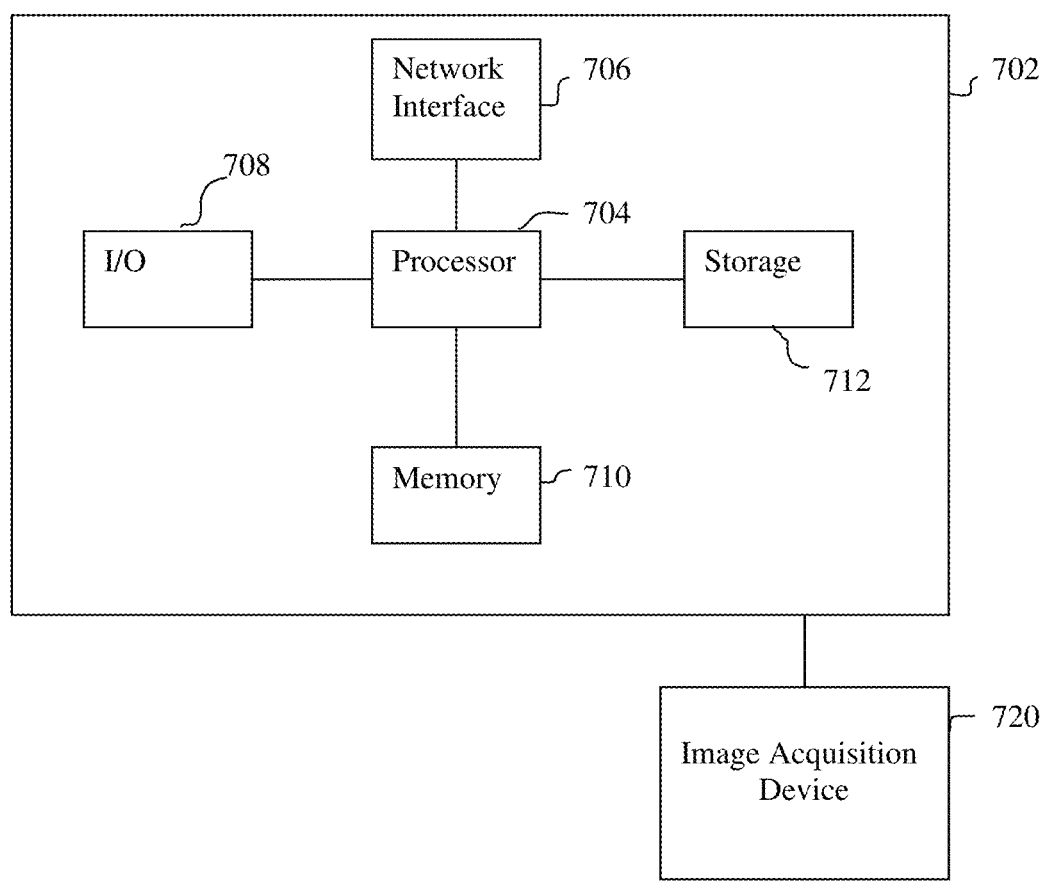
FIG. 7 is a high-level block diagram of a computer capable of implementing the present invention.

The above-described methods may be implemented on a computer using well-known computer processors, memory units, storage devices, computer software, and other components. A high-level block diagram of such a computer is illustrated in FIG. 7. Computer 702 contains a processor 704, which controls the overall operation of the computer 702 by executing computer program instructions which define such operation. The computer program instructions may be stored in a storage device 712 (e.g., magnetic disk) and loaded into memory 710 when execution of the computer program instructions is desired. Thus, the steps of the methods of FIGS. 1, 3, 5, and 6 may be defined by the computer program instructions stored in the memory 710 and/or storage 712 and controlled by the processor 704 executing the computer program instructions. An image acquisition device 720, such as a CT scanning device, MR scanning device, Ultrasound device, etc., can be connected to the computer 702 to input image data to the computer 702. The image acquisition device 720 and the computer 702 may communicate wirelessly through a network. The computer 702 also includes one or more network interfaces 706 for communicating with other devices via a network. The computer 702 also includes other input/output devices 708 that enable user interaction with the computer 702 (e.g., display, keyboard, mouse, speakers, buttons, etc.). One skilled in the art will recognize that an implementation of an actual computer could contain other components as well, and that FIG. 7 is a high level representation of some of the components of such a computer for illustrative purposes.

The above-described methods may be implemented using computers operating in a client-server relationship. Typically, in such a system, the client computers are located remotely from the server computer and interact via a network. The client-server relationship may be defined and controlled by computer programs running on the respective client and server computers.

The above-described methods may be implemented within a network-based cloud computing system. In such a network-based cloud computing system, a server or another processor that is connected to a network communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc. For example, the server may transmit a request adapted to cause a client computer to perform one or more of the method steps described herein, including one or more of the steps of FIGS. 1, 3, 5, and 6. Certain steps of the methods described herein, including one or more of the steps of FIGS. 1, 3, 5, and 6 may be performed by a server or by another processor in a network-based cloud-computing system. Certain steps of the methods described herein, including one or more of the steps of FIGS. 1, 3, 5, and 6, may be performed by a client computer in a network-based cloud computing system. The steps of the methods described herein, including one or more of the steps of FIGS. 1, 3, 5, and 6, may be performed by a server and/or by a client computer in a network-based cloud computing system, in any combination.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for simulating blood flow to estimate one or more hemodynamic measures of interest for a patient, comprising:
   generating a patient-specific anatomical model of vessels of a patient based on patient data;
   receiving one or more continuous cardiovascular measurements of the patient from a wearable sensor network on the patient;
   personalizing a computational blood flow model for simulating blood flow in the patient-specific anatomical model of the vessels of the patient by personalizing arterial wall properties, an inlet boundary condition, and outlet boundary conditions of the computational blood flow model based on the one or more continuous cardiovascular measurements from the wearable sensor network, wherein the inlet boundary condition is personalized by estimating a continuous cardiac output based on the one or more continuous cardiovascular measurements and scaling a population-averaged aortic inlet profile using the estimated continuous cardiac output to generate a personalized time-varying flow rate profile at an aortic inlet;
   simulating blood flow and pressure in the patient-specific anatomical model of the vessels of the patient using the personalized computational blood flow model; and computing one or more hemodynamic measures of interest for the patient based on the simulated blood flow and pressure.

2. The method of claim 1, wherein generating a patient-specific anatomical model of vessels of a patient based on patient data comprises:
receiving medical image data of the patient; and
extracting centerlines and cross-sectional measurements for each of a plurality of arteries in a full-body systemic arterial model from the medical image data of the patient.

3. The method of claim 1, wherein generating a patient-specific anatomical model of vessels of a patient based on patient data comprises:
initializing a full-body systemic arterial model using a population-averages full-body systemic arterial model; and
personalizing lengths and radii of a plurality of arteries in the full-body systemic arterial model based on the patient data.

4. The method of claim 3, wherein personalizing lengths and radii of a plurality of arteries in the full-body systemic arterial model based on the patient data comprises:
personalizing the lengths and radii of the plurality of arteries in the systemic arterial model based on height, weight, body mass index, gender, length of arms, length of legs, length of neck, and length of head of the patient.

5. The method of claim 1, further comprising repeating the receiving, personalizing, simulating, and computing steps each time a specified time period has passed, wherein receiving one or more continuous cardiovascular measurements of the patient from a wearable sensor network on the patient comprises:
receiving the one or more continuous cardiovascular measurements of the patient acquired by the wearable sensor network on the patient during the specified time period.

6. The method of claim 1, wherein receiving one or more continuous cardiovascular measurements of the patient from a wearable sensor network on the patient comprises:
receiving continuous heart rate measurements, continuous electrocardiogram (ECG) signals, and one or more of continuous pulse oximetry measurements or continuous blood pressure measurements from the wearable sensor network.

7. The method of claim 6, wherein the patient-specific anatomical model of the vessels of the patient is a patient-specific anatomical model of full-body system arterial geometry and the computational blood flow model represents arteries in the patient-specific anatomical model using one-dimensional models.

8. The method of claim 7, wherein personalizing a computational blood flow model for simulating blood flow in the patient-specific anatomical model of the vessels of the patient by personalizing arterial wall properties, an inlet boundary condition, and outlet boundary conditions of the computational blood flow model based on the one or more continuous cardiovascular measurements from the wearable sensor network comprises:
personalizing wall properties based on the continuous pulse oximetry measurements or the continuous blood pressure measurements and the continuous ECG signals.

9. The method of claim 7, wherein estimating a continuous cardiac output based on the one or more continuous cardiovascular measurements and scaling a population-averaged aortic inlet profile using the estimated continuous cardiac output to generate a personalized time-varying flow rate profile at an aortic inlet comprises:
estimating the continuous cardiac output based on the continuous pulse oximetry measurements and the continuous ECG signals and scaling the population-averaged aortic inlet profile using the estimated cardiac output and the continuous heart rate measurements to generate the personalized time-varying flow rate profile at the aortic inlet.

10. The method of claim 7, wherein personalizing a computational blood flow model for simulating blood flow in the patient-specific anatomical model of the vessels of the patient by personalizing arterial wall properties, an inlet boundary condition, and outlet boundary conditions of the computational blood flow model based on the one or more continuous cardiovascular measurements from the wearable sensor network comprises:
estimating three-element Windkessel parameters at outlets of the patient-specific anatomical model of full-body system arterial geometry based on the one or more continuous cardiovascular measurements from the wearable sensor network.

11. The method of claim 1, wherein computing one or more hemodynamic measures of interest for the patient based on the simulated blood flow and pressure comprises:
computing one or more of a central aortic blood pressure measure, a severity of peripheral artery disease (PAD) measure, a severity of aortic coarctation measure, an onset of hypertension measure, a cardiovascular disease (CVD) risk prediction measure, and a severity of coronary artery disease measure based on the simulated blood flow and pressure.

12. The method of claim 1, further comprising:
comparing at least one of the one or more hemodynamic measures of interest to a corresponding hemodynamic measure of interest acquired for a population of other patients to detect deviations from population-averaged values.

13. An apparatus for simulating blood flow to estimate one or more hemodynamic measures of interest for a patient, comprising:
means for generating a patient-specific anatomical model of vessels of a patient based on patient data;
means for receiving one or more continuous cardiovascular measurements of the patient from a wearable sensor network on the patient;
means for personalizing a computational blood flow model for simulating blood flow in the patient-specific anatomical model of the vessels of the patient by personalizing arterial wall properties, an inlet boundary condition, and outlet boundary conditions of the computational blood flow model based on the one or more continuous cardiovascular measurements from the wearable sensor network, wherein the inlet boundary condition is personalized by estimating a continuous cardiac output based on the one or more continuous cardiovascular measurements and scaling a population-averaged aortic inlet profile using the estimated continuous cardiac output to generate a personalized time-varying flow rate profile at an aortic inlet;
means for simulating blood flow and pressure in the patient-specific anatomical model of the vessels of the patient using the personalized computational blood flow model; and means for computing one or more hemodynamic measures of interest for the patient based on the simulated blood flow and pressure.

14. The apparatus of claim 13, wherein the means for generating a patient-specific anatomical model of vessels of a patient based on patient data comprises:
   means for extracting centerlines and cross-sectional measurements for each of a plurality of arteries in a full-body systemic arterial model from medical image data of the patient.

15. The apparatus of claim 13, wherein the means for generating a patient-specific anatomical model of vessels of a patient based on patient data comprises:
   means for initializing a full-body systemic arterial model using a population-averages full-body systemic arterial model; and
   means for personalizing lengths and radii of a plurality of arteries in the full-body systemic arterial model based on the patient data.

16. The apparatus of claim 13, wherein the one or more continuous cardiovascular measurements of the patient from the wearable sensor network comprise continuous heart rate measurements, continuous electrocardiogram (ECG) signals, and one or more of continuous pulse oximetry measurements or continuous blood pressure measurements from the wearable sensor network.

17. The apparatus of claim 16, wherein the patient-specific anatomical model of the vessels of the patient is a patient-specific anatomical model of full-body system arterial geometry and the computational blood flow model represents arteries in the patient-specific anatomical model using one-dimensional models.

18. The apparatus of claim 13, wherein the means for computing one or more hemodynamic measures of interest for the patient based on the simulated blood flow and pressure comprises:
   means for computing one or more of a central aortic blood pressure measure, a severity of peripheral artery disease (PAD) measure, a severity of aortic coarctation measure, an onset of hypertension measure, a cardiovascular disease (CVD) risk prediction measure, and a severity of coronary artery disease measure based on the simulated blood flow and pressure.

19. A non-transitory computer readable medium storing computer program instructions for simulating blood flow to estimate one or more hemodynamic measures of interest for a patient, the computer program instructions when executed by a processor cause the processor to perform operations comprising:
   generating a patient-specific anatomical model of vessels of a patient based on patient data;
   receiving one or more continuous cardiovascular measurements of the patient from a wearable sensor network on the patient;
   personalizing a computational blood flow model for simulating blood flow in the patient-specific anatomical model of the vessels of the patient by personalizing arterial wall properties, an inlet boundary condition, and outlet boundary conditions of the computational blood flow model based on the one or more continuous cardiovascular measurements from the wearable sensor network, wherein the inlet boundary condition is personalized by estimating a continuous cardiac output based on the one or more continuous cardiovascular measurements and scaling a population-averaged aortic inlet profile using the estimated continuous cardiac output to generate a personalized time-varying flow rate profile at an aortic inlet;
   simulating blood flow and pressure in the patient-specific anatomical model of the vessels of the patient using the personalized computational blood flow model; and
   computing one or more hemodynamic measures of interest for the patient based on the simulated blood flow and pressure.

20. The non-transitory computer readable medium of claim 19, wherein generating a patient-specific anatomical model of vessels of a patient based on patient data comprises:
   receiving medical image data of the patient; and
   extracting centerlines and cross-sectional measurements for each of a plurality of arteries in a full-body systemic arterial model from the medical image data of the patient.

21. The non-transitory computer readable medium of claim 19, wherein generating a patient-specific anatomical model of vessels of a patient based on patient data comprises:
   initializing a full-body systemic arterial model using a population-averages full-body systemic arterial model; and
   personalizing lengths and radii of a plurality of arteries in the full-body systemic arterial model based on the patient data.

22. The non-transitory computer readable medium of claim 19, wherein the operations further comprise repeating the receiving, personalizing, simulating, and computing steps each time a specified time period has passed, wherein receiving one or more continuous cardiovascular measurements of the patient from a wearable sensor network on the patient comprises:
   receiving the one or more continuous cardiovascular measurements of the patient acquired by the wearable sensor network on the patient during the specified time period.

23. The non-transitory computer readable medium of claim 19, wherein receiving one or more continuous cardiovascular measurements of the patient from a wearable sensor network on the patient comprises:
   receiving continuous heart rate measurements, continuous electrocardiogram (ECG) signals, and one or more of continuous pulse oximetry measurements or continuous blood pressure measurements from the wearable sensor network.

24. The non-transitory computer readable medium of claim 23, wherein the patient-specific anatomical model of the vessels of the patient is a patient-specific anatomical model of full-body system arterial geometry and the computational blood flow model represents arteries in the patient-specific anatomical model using one-dimensional models.

25. The non-transitory computer readable medium of claim 24, wherein personalizing a computational blood flow model for simulating blood flow in the patient-specific anatomical model of the vessels of the patient by personalizing arterial wall properties, an inlet boundary condition, and outlet boundary conditions of the computational blood flow model based on the one or more continuous cardiovascular measurements from the wearable sensor network comprises:
   personalizing wall properties based on the continuous pulse oximetry measurements or the continuous blood pressure measurements and the continuous ECG signals.

26. The non-transitory computer readable medium of claim 24, wherein estimating a continuous cardiac output based on the one or more continuous cardiovascular measurements and scaling a population-averaged aortic inlet profile using the estimated continuous cardiac output to generate a personalized time-varying flow rate profile at an aortic inlet comprises:
 estimating the continuous cardiac output based on the continuous pulse oximetry measurements and the continuous ECG signals and scaling the population-averaged aortic inlet profile using the estimated cardiac output and the continuous heart rate measurements to generate the personalized time-varying flow rate profile at the aortic inlet.

27. The non-transitory computer readable medium of claim 24, wherein personalizing a computational blood flow model for simulating blood flow in the patient-specific anatomical model of the vessels of the patient by personalizing arterial wall properties, an inlet boundary condition, and outlet boundary conditions of the computational blood flow model based on the one or more continuous cardiovascular measurements from the wearable sensor network comprises:
 estimating three-element Windkessel parameters at outlets of the patient-specific anatomical model of full-body system arterial geometry based on the one or more continuous cardiovascular measurements from the wearable sensor network.

28. The non-transitory computer readable medium of claim 19, wherein computing one or more hemodynamic measures of interest for the patient based on the simulated blood flow and pressure comprises:
 computing one or more of a central aortic blood pressure measure, a severity of peripheral artery disease (PAD) measure, a severity of aortic coarctation measure, an onset of hypertension measure, a cardiovascular disease (CVD) risk prediction measure, and a severity of coronary artery disease measure based on the simulated blood flow and pressure.

29. The non-transitory computer readable medium of claim 19, wherein the operations further comprise:
 comparing at least one of the one or more hemodynamic measures of interest to a corresponding hemodynamic measure of interest acquired for a population of other patients to detect deviations from population-averaged values.

* * * * *